United States Patent
Suzuki et al.

(10) Patent No.: US 6,958,229 B2
(45) Date of Patent: *Oct. 25, 2005

(54) METHOD FOR PRODUCING HIGHLY UNSATURATED FATTY ACIDS AND LIPID CONTAINING SAME

(75) Inventors: Osamu Suzuki, Higashihiroshima (JP); Kazuhisa Ono, Higashihiroshima (JP); Seiko Shigeta, Hiroshima (JP); Tsunehiro Aki, Higashihiroshima (JP); Kengo Akimoto, Osaka (JP)

(73) Assignee: Suntory Limited, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/389,318

(22) Filed: Sep. 3, 1999

(65) Prior Publication Data

US 2002/0146784 A1 Oct. 10, 2002

(30) Foreign Application Priority Data

Mar. 4, 1997 (JP) .............................. 9-049337
Mar. 4, 1998 (WO) ............................... PCT/JP98/00891

(51) Int. Cl.$^7$ .................................................. C12P 7/64
(52) U.S. Cl. ..................... 435/134; 435/135; 435/254.1
(58) Field of Search ................... 435/134, 135, 435/254.1

(56) References Cited

U.S. PATENT DOCUMENTS 5,583,019 A 12/1996 Barclay
5,658,767 A * 8/1997 Kyle ........................... 435/134

FOREIGN PATENT DOCUMENTS

| EP | 0252716 | 1/1988 |
| EP | 0726321 | 8/1996 |
| JP | 63-14697 | 1/1988 |
| JP | 5-91887 | 4/1993 |
| JP | 6-153970 | 6/1994 |
| JP | 8-214893 | 8/1996 |

OTHER PUBLICATIONS

A. Singh et al, "Production of high yields of arachidonic acid in a fed–batch system by *Mortierella alpina* ATCC 32222," Appl. Microbiol. Biotechnol., 48, 1997, pp. 1–5.

Z. Li et al., *The Canadian Journal of Chemical Engineering*, 73:135–139 (1995).

Li et al., *The Canadian Journal of Chemical Engineering*, 73:135–139 (1995).

Totani et al., *Industrial Production of Arachidonic Acid by Mortierella*, Chapter 4, pp. 52–60.

* cited by examiner

Primary Examiner—Irene Marx
(74) Attorney, Agent, or Firm—Buchanan Ingersoll PC

(57) ABSTRACT

A method for producing highly unsaturated fatty acids comprising culturing a microorganism, belonging to the genus *Mortierella* and having resistance to a carbon source, in a medium having a carbon source concentration of at least 4% by weight, and collecting highly unsaturated fatty acids from the cultured products. Culturing the microorganism for about a week gives at least about 7 g/L of highly unsaturated fatty acids.

2 Claims, No Drawings

METHOD FOR PRODUCING HIGHLY UNSATURATED FATTY ACIDS AND LIPID CONTAINING SAME

FIELD OF THE INVENTION

The present invention relates to a microorganism, belonging to the genus *Mortierella* and having resistance to a carbon source of high concentration, a method for the production of arachidonic acid, dihomo-γ-linolenic acid and/or eicosapentaenoic acid, and of a lipid containing the acids by fermentation using the microorganism, as well as animal feed containing the microorganism.

BACKGROUND ART

Attention has been paid to arachidonic acid (5,8,11,14-eicosatetraenoic acid), dihomo-y-linolenic acid (8,11,14-eicosatrienoic acid) and eicosapentaenoic acid (5,8,11,14, 17-eicosapentaenoic acid) because these acids can become precursors of eicosanoids such as prostaglandin, leukotriene and tromboxane, and because the acids themselves have physiological activities. For example, eicosapentaenoic acid has been marketed as a food and medicine on the basis of its antithrombotic preventive action or lipid-lowering action.

Furthermore, it has recently been disclosed that arachidonic acid is similar to docosahexaenoic acid in that it is contained in breast milk, and that arachidonic acid is useful for growing infants ("Advances in Polyunsaturated Fatty Acid Research," Elsevier Science Publishers, 1993, pp261–264). It has further been disclosed that arachidonic acid is important in the growth of the height and of the brain of embryos (Proc. Natl. Acad. Sci. USA, 90, 1073–1077 (1993), Lancet, 344, 1319–1322 (1994)).

Methods for producing such acids as arachidonic acid, dihomo-γ-linolenic acid or eicosapentaenoic acid in higher yields than conventional methods have been developed using microorganisms belonging to the genus *Mortierella* (Japanese Examined Patent Publication (Kokoku) No. 7-34752, Japanese Unexamined Patent Publication (Kokai) No. 6-153970, Japanese Unexamined Patent Publication (Kokai) No. 8-214893, Chapter 4 in Industrial Applications of Single Cell Oil, ed. by D. J. Kyle and C. Ratledge, American Oil Chemists' Society, Illinois, 1992, WO96/21037, Japanese Examined Patent Publication (Kokoku) No. 7-22513, Japanese Examined Patent Publication (Kokoku) No. 7-12315, and Japanese Unexamined Patent Publication (Kokai) No. 1-243992).

However, the microorganisms belonging to the genus *Mortierella* which have been used in the methods each have a low resistance to a high glucose concentration. Fed-batch culture is therefore practiced currently in the actual industrial production by culturing with aeration and agitation, so that the glucose concentration is in the range of 2 to 4% by weight. Accordingly, the methods have the problem that the production steps become complicated. Moreover, the microorganism belonging to the genus *Mortierella*, subgenus *Mortierella* which has heretofore been used for producing arachidonic acid, dihomo-γ-linolenic acid or eicosapentaenoic acid evidently shows a low growth level of microorganism (dried weight of the microbial cells per medium), as compared with a microorganism belonging to the genus *Mortierella*, subgenus *Micromucor* which has been used for producing γ-linolenic acid. As a result, the production amount of lipid containing highly unsaturated fatty acids per medium has been low (for example, the growth level of *Mortierella alpina* belonging to the subgenus *Mortierella* is 22.5 g/L, whereas that of *Mortierella ramanniana* var. *angulispora* belonging to the subgenus *Micromucor* reaches 79 g/L (Chapter 5, Chapter 7 in Industrial Applications of Single Cell Oil, ed. by D. J. Kyle and C. Ratledge, American Oil Chemists' Society, Illinois, 1992)).

The productivity of arachidonic acid by a microorganism belonging to the genus *Mortierella*, subgenus *Mortierella* has heretofore been disclosed, for example, as explained below. Japanese Unexamined Patent Publication (Kokai) No. 6-15397 discloses in an example that the microorganism produced 4.09 g/L of arachidonic acid after culturing for 7 days while the initial glucose concentration had been determined to be 2%. Moreover, Japanese Unexamined Patent Publication (Kokai) No. 8-214893 discloses in an example that the microorganism produced 2.3 g/L of arachidonic acid after culturing for 3 days while the initial glucose concentration had been determined to be 4.3%.

An example in which the concentration of a carbon source was increased will be explained below. The experimental results in chapter 4 of "Industrial Applications of Single Cell Oil, ed. by D. J. Kyle and C. Ratledge, American Oil Chemists' Society, Illinois, 1992" are as follows: 1.5 g/L of arachidonic acid was produced after culturing for 7 days while the initial dextrose concentration had been determined to be 9.8%; and 9.1 g/L of arachidonic acid was produced after culturing for 16 days while the initial dextrose concentration had been determined to be 9.8%. The growth of the microorganism was particularly poor due to a high initial dextrose concentration, and the production amount of arachidonic acid after culturing for 7 days was as low as only 1.5 g/L; the culturing period was determined to be 16 days for the purpose of ensuring the production amount.

Furthermore, in an example of WO96/21037, 5.3 g/L of arachidonic acid was produced after culturing for 8 days while the initial glucose concentration had been determined to be 10%. However, in order to suppress the inhibition of the growth of the microorganism caused by the high glucose concentration, procedures such as pH control and addition of salts were fully utilized, and complicated operations were required.

As explained above, for the production of substances by fermentation using microorganisms, in general, procedures such as a procedure in which the growth amount of the microorganism is increased and a procedure in which the production amount per microorganism is increased are taken when the productivity is intended to be enhanced. Increasing the concentration of the carbon source which is to become the nutrition source for growing the microorganism leads the microorganism to increase the growth amount, and culturing at a carbon source concentration as high as possible is preferred. On the other hand, however, increasing the concentration of the carbon source produces a harsh condition for growing the microorganism due to the resultant osmotic pressure, and results in suppressing the growth thereof.

As described above, the example wherein growth of the microorganism becomes poor when the initial glucose concentration is increased, and the production amount of arachidonic acid is as low as about 1.5 g/L after culturing for 7 days, and the example wherein the medium is adjusted by procedures such as controlling the pH and adding salts for the purpose of increasing the initial glucose concentration can also be regarded as examples showing difficulties of producing a substance by fermentation using a microorganism.

Accordingly, it has been desired to develop a method for producing arachidonic acid, dihomo-γ-linolenic acid or eicosapentaenoic acid efficiently with simple operations and in a large amount by finding a microorganism which is resistant to a carbon source of high concentration at the starting stage and which shows a sufficient growth level even in a medium having a high initial glucose concentration, and using the microorganism.

DISCLOSURE OF THE INVENTION

Accordingly, the present invention is intended to provide a method for efficiently producing arachidonic acid, dihomo-γ-linolenic acid and/or eicosapentaenoic acid, or a lipid containing said acids, by utilizing a microorganism belonging to the genus *Mortierella* and having resistance to a carbon source of high concentration; a microorganism belonging to the genus *Mortierella* and having resistance to a carbon source of high concentration; and animal feed containing the microorganism.

As a result of doing various studies to achieve the objects as mentioned above, the present inventors have discovered microorganisms belonging to the genus *Mortierella* which have resistance to a carbon source of high concentration, which show a high growth level even in a medium having a high carbon source concentration at the start of culturing, and which consequently exhibit high productivity of arachidonic acid, dihomo-γ-linolenic acid and/or eicosapentaenoic acid, or lipid containing these acids, the present invention thus having been achieved.

More specifically, the present inventors have discovered a new microorganism belonging to the genus *Mortierella* and having the following properties: the microorganism shows a high growth level without using complicated operations such as pH control and addition of inorganic salts, in a simple medium containing glucose as a carbon source and yeast extract, etc., as a nitrogen source, having a carbon source concentration of at least 4% by weight, more specifically, having a carbon source concentration of at least 8% by weight, even having a carbon source concentration of at least 11%, and as a result produces with high productivity arachidonic acid, dihomo-γ-linolenic acid and/or eicosapentaenoic acid or lipid containing the acids. The present invention thus has been achieved. Note that, at 4% by weight of carbon source concentration, conventional microorganisms belonging to the genus *Mortierella*, subgenus *Mortierella* (such as *Mortierella alpina* IFO 8568) and having been conventionally used for the production of arachidonic acid, dehomo-γ-linolenic acid and/or eicosapentaenoic acid lower their growth level, and at 8% by weight of carbon source concentration, the above-mentioned conventional microorganisms cannot grow.

The present invention therefore provides a process for producing arachidonic acid or a lipid containing arachidonic acid comprising the steps of culturing a microorganism belonging to the genus *Mortierella* and having resistance to a carbon source of high concentration in a medium having a carbon source concentration of at least 4% by weight at the start of culturing, thereby forming arachidonic acid or lipid containing arachidonic acid, and recovering arachidonic acid or lipid containing arachidonic acid.

That is, according to the present invention, a microorganism belonging to the genus *Mortierella* and having resistance to a carbon source of high concentration is cultured in a medium having a carbon source concentration of at least 4% by weight at the start of culturing, whereby at least 7 g/L of arachidonic acid can be produced after culturing for 8 days. The productivity of arachidonic acid can further be improved by further increasing the carbon source concentration at the start of culturing and feeding a carbon source during culturing. For example, at least about 10 g/L of arachidonic acid can be produced when the carbon source concentration is at least 8% by weight at the start of culturing, and at least about 14 g/L of arachidonic acid can be produced when the carbon source concentration is at least 11% by weight at the start thereof. The productivity is about 3 times as much as the productivity 5.3 g/L of arachidonic acid shown by a microorganism belonging to the genus *Mortierella* which has heretofore been known (WO96/21037).

The present invention also provides a process for producing dihomo-γ-linolenic acid or lipid containing dihomo-γ-linolenic acid comprising the steps of culturing a microorganism belonging to the genus *Mortierella* and having resistance to a carbon source of high concentration in a medium containing a Δ5 desaturase inhibitor, thereby forming dihomo-γ-linolenic acid or lipid containing dihomo-γ-linolenic acid, and recovering dihomo-γ-linolenic acid or lipid containing dihomo-γ-linolenic acid.

The present invention also provides a process for producing eicosapentaenoic acid or lipid containing eicosapentaenoic acid comprising the steps of culturing at temperatures of up to 20° C. a microorganism belonging to the genus *Mortierella* and having resistance to a carbon source of high concentration, thereby forming eicosapentaenoic acid or lipid containing eicosapentaenoic acid, and recovering eicosapentaenoic acid or lipid containing eicosapentaenoic acid.

The present invention also provides animal feed comprising a microorganism belonging to the genus *Mortierella* and having resistance to a carbon source of high concentration.

The present invention also provides the genus *Mortierella,* such as strain SAM 2197 (FERM BP-6261), having resistance to a carbon source of high concentration.

EMBODIMENTS FOR CARRYING OUT THE INVENTION

The microorganism used in the present invention which belongs to the genus *Mortierella* and which has resistance to a carbon source of high concentration is a microorganism belonging to the genus *Mortierella,* and has the ability to produce at least 7 g/L of arachidonic acid per medium when the microorganism is conventionally cultured by culturing with aeration and agitation for 2 to 12 days, preferably for 5 to 12 days, more preferably for 5 to 10 days, using a liquid medium having, at the start of culturing, a carbon source concentration of at least 4%, preferably at least 8%, more preferably at least 11%, and a nitrogen source concentration of at least 2%.

The use of a microorganism belonging to the genus *Mortierella* and having such properties can produce dihomo-γ-linolenic acid or eicosapentaenoic acid in addition to arachidonic acid in a higher yield than the use of conventional microorganisms, though the production depends on the culturing conditions and additives in the medium.

The genus *Mortierella* is known to include subgenus *Mortierella* and subgenus *Micromucor*. A microorganism belonging to subgenus *Mortierella* is desirable for the production of arachidonic acid, dihomo-γ-linolenic acid and/or eicosapentaenoic acid.

Furthermore, subgenus *Mortierella* is known to include section *Alpina,* section *Hygrophila,* section *Mortierella,* section *Schmuckeri,* section *Simplex,* section *Spinosa* and section *Stylospora*. A microorganism belonging to section *Alpina* is desirable for the production of arachidonic acid, dihomo-γ-linolenic acid and/or eicosapentaenoic acid.

Moreover, the section *Alpina* is known to include species *alpina* and species *alliacea*; the section *Hygrophila* is known to include species *elongata* and species *minutissima*; the section *Mortierella* is known to include species *polycephala*; and the section *Stylospora* is known to include species *verticillata*.

A microorganism which was isolated from soil by the present inventors and internationally deposited under Budapest Treaty as *Mortierella* sp., strain SAM 2197 (FERM BP-6261) on Mar. 3, 1997 at National Institute of Bioscience and Human-Technology Agency of Industrial Science and Technology (1-3, Higashi 1-chome, Tsukuba-City, Ibaragi Prefecture) can be used as a concrete strain.

*Mortierella* sp., strain SAM 2197 has microbial properties as described below.

Culturing Behavior (Culturing in the Darkness at 25° C. for 5 Days)

A LcA medium (1 g glucose, 1 g $KH_2PO_4$, 0.2 g $MgSO_4 \cdot 7H_2O$, 0.2 g KCl, 2 g $NaNO_3$, 0.2 g yeast extract, 13 g agar and 1,000 ml distilled water, pH 6.5 to 7.0): the colony having a diameter of 65 mm, having a white color, and slightly forming eareal hypha.

A corn meal agar medium (manufactured by Difco, catalogue No. 0386-02-2): the colony having a diameter of 50 mm, somewhat showing a rose petal-like shape, having a white color, and slightly forming eareal hypha.

Morphological Properties

Sporangiophores are formed from eareal hypha. The sporangiophores each have a length of 60 to 120 $\mu$m. The sporangiophores each do not branch. The sporangiophores each become thin from the base portion toward the tip, and they each slightly increase in width immediately below the sporangium. The base bottom portion of each of the sprangiophores often swells in an irregular form. A colorless sporangium is formed at the tip of each of the sprangiophores. A distinct color is observed at the tip of each of the sprangiophores which the sprangium has left. The sporangium contains several or many sporangiospores.

A sporangium containing many sporangiospores is subspherical, and has a diameter of about 15 $\mu$m. The sporangiospore is unicellular, elliptic and colorless, has a length of 3 to 5 $\mu$m, and a width of 1.5 to 2.5 $\mu$m. A sporangium containing several sporangiospores has an irregular shape, and form a thick membrane spores (having a thin wall) in an elliptic, sub-spherical or irregular form.

Strain SAM 2197 has been identified from the results as mentioned above to belong to the genus *Mortierella*, sub-genus *Mortierella*.

The microorganism of the present invention, belonging to the genus *Mortierella* and having resistance to a carbon source of high concentration, can be cultured under the culturing conditions and by the culturing methods as described below.

In order to culture the strain used in the present invention, spores of hyphae of the strain, or a preculture obtained by culturing in advance is inoculated into a liquid or solid medium, and cultured. When a liquid medium is used, glucose, fructose, xylose, saccharose, maltose, soluble starch, molasses, glycerol, mannitol, citric acid, corn starch, and the like, which are generally used, can be each used as a carbon source. Glucose, fructose, maltose, glycerol, citric acid and corn starch are particularly preferred.

Examples of the nitrogen source which is commonly used include organic nitrogen sources such as urea and inorganic nitrogen sources such as sodium nitrate, ammonium nitrate and ammonium sulfate, in addition to natural nitrogen sources such as peptone, yeast extract, malt extract, meat extract, Casamino acid, corn steep liquor and soybean protein. Moreover, any of the conventionally used minor nutrition sources such as mentioned below can be used optionally: phosphates such as potassium phosphate and potassium dihydrogenphosphate; inorganic salts such as ammonium sulfate, sodium sulfate, magnesium sulfate, iron sulfate, copper sulfate, magnesium chloride and potassium chloride; and vitamins.

Moreover, in the present invention, addition of a substrate for desired arachidonic acid, dihomo-$\gamma$-linolenic acid and/or eicosapentaenoic acid to the medium can promote accumulation of the highly unsaturated fatty acids. Examples of the substrate include hydrocarbons such as hexadecane or octadecane; fatty acids such as oleic acid or linolic acid, or their salts such as sodium salts or potassium salts; fatty esters such as ethyl esters, fatty esters of glycerin or fatty esters of sorbitan; and fats and oils such as olive oil, soybean oil, rapeseed oil, cottonseed oil or coconut oil. These substances can be used singly or in combination. However, the substrate is not restricted to these substances. A total amount of the substrate added is from 0.001 to 10% by weight, preferably from 0.5 to 10% by weight based on the medium. Moreover, the culturing can also be conducted with one of these substrates used as the sole carbon source. In such a case, amount of the substrate added is further increased if necessary.

The medium components such as carbon sources, nitrogen sources, inorganic salts, vitamins and/or substrates can be added to the medium prior to starting culturing and/or to the culture medium during culturing. These components can be added once, or continuously, or at a plurality of times with the lapse of time. These medium components can be added each independently, or as a mixture prepared in advance. Of the medium components, medium components such as inorganic salts, vitamins and/or substrates are not particularly restricted so long as the concentrations thereof do not hamper the growth of the microorganism. The medium components can be used each in a conventionally used concentration range.

On the other hand, the carbon source concentration of the medium at the start of culturing is to be at least 4% by weight, preferably at least 8% by weight, more preferably at least 11% by weight. As a result, the culturing operation can be simplified. Moreover, because it becomes possible to feed a carbon source having a concentration of at least 2% by weight, preferably at least 4% by weight, more preferably at least 6% by weight, if the carbon source is added to a culture medium in which a microorganism is being cultured, still more efficient growth of the microorganism and production of desired highly unsaturated fatty acids can be performed.

A total amount of the nitrogen source added should be from 0.01 to 10% by weight, preferably from 0.1 to 10% by weight. A medium at the start of culturing can have a nitrogen source concentration of at least 2% by weight, and a nitrogen source can also be fed to the culture medium in the course of culturing.

The culturing temperature is from 5 to 40° C., preferably from 20 to 30° C. The microbial cells are grown by culturing at temperatures of 20 to 30° C., and desired highly unsaturated fatty acids are produced by continuing culturing at temperatures of 5 to 20° C. Such temperature control can raise the ratio of the highly unsaturated fatty acids to the fatty acids thus formed. The pH of the medium is not required to be particularly controlled, but it is in the range of 4 to 10 which is usually used, preferably 6 to 9; culturing is conducted by culturing with aeration and agitation, culturing with shaking or static culturing. In particular, culturing with aeration and agitation using a liquid medium is preferred for efficient production of the desired highly unsaturated fatty acids. The culturing is carried out usually for 2 to 12 days, preferably for 5 to 12 days, more preferably for 5 to 10 days.

Eicosapentaenoic acid can be produced by using the culturing temperature to be up to 20° C. from the start of culturing or in the course thereof. Moreover, addition of α-linolenic acid which is a precursor of eicosapentaenoic acid or such lipid containing α-linolenic acid as linseed oil or perilla oil to the medium results in efficient production of eicosapentaenoic acid, and its production is further improved when the culturing temperature is up to 20° C.

When the microorganism is cultured by solid culturing, wheat bran, chaff, rice bran, or the like to which from 50 to 100% by weight of water based on the solid substance weight is added is used, and a microorganism is cultured for 3 to 14 days at temperatures of from 5 to 40° C., preferably at temperatures as mentioned above; nitrogen sources, inorganic salts and minor nutrient sources can optionally be added.

Furthermore, in order to increase the production amount of dihomo-γ-linolenic acid, it is preferred to culture a microorganism of the present invention in the presence of a Δ5 desaturase inhibitor. Examples of the Δ5 desaturase inhibitor include lignan compounds such as sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]octane or 2-(3,4-methylenedioxyphenyl)-6-(3-methoxy-4-hydroxyphenoxy)-3,7-dioxabicyclo [3.3.0]octane; piperonylbutoxide; curcumin; sesame oil; peanut oil; extract of herbs such as tarragon, dill seed, parsley, turmeric and nutmeg; extract of Alaliacea; extract of paulownia; extract of bark of HAKKA; extract of HIHATSU; extract of SAISHIN; and extract of sesame oil, by-products in the production step of sesame oil (such as defatted cake of sesame seed and deodorized scum of sesame oil), sesame seed, and the like.

In addition, extract of sesame oil, by-products in the production of sesame oil (such as defatted cake of sesame seed and deodorized scum of sesame oil), sesame seed, and the like can be prepared with various organic solvents which are substantially immiscible with sesame oil and which can extract and dissolve components having an inhibition activity for Δ5 desaturase. Examples of such organic solvents include acetone, methyl ethyl ketone, diethyl ketone, methanol and ethanol. Moreover, not only solvent-extracted substances but also those substances which are separated by steam distillation and molecular distillation are included in the extract. Furthermore, the extract of herbs can be prepared with conventional solvents such as dichloromethane, ethanol, methanol and ethyl ether.

The addition amount of the Δ5 desaturase inhibitor in the medium is approximately as described below. A total addition amount of sesame oil or peanut oil, or both sesame oil and peanut oil is from 0.001 to 10% by weight, preferably from 0.5 to 10% by weight based on the medium. When the extract of sesame oil, by-products in the production step of sesame oil (such as defatted cake of sesame seed and deorderized scum of sesame oil), sesame seed, and the like is added, the addition amount is from $3 \times 10^{-3}$ to $3 \times 10^{-1}$% by weight based on the medium.

Furthermore, when lignan compounds such as sesamin, sesaminol, episesamin and episesaminol are added, the addition amount (referring to a total amount when a combination of at least two of these substances is used) is from $1 \times 10^{-3}$ to $1 \times 10^{-1}$% by weight based on the medium. These additives can be added to the medium prior to or immediately after inoculating the microorganism to be produced, or to the medium immediately after starting culturing, or the additives can also be added at both times mentioned above. Addition of the additives subsequent to starting culturing can be conducted once, or at a plurality of times intermittently.

When culturing is carried out as explained above, lipid containing large amounts of arachidonic acid, dihomo-γ-linolenic acid and/or eicosapentaenoic acid is formed and intracellularly accumulated.

Desired highly unsaturated fatty acids can be obtained by conventional procedures from a culture medium in the course of producing a lipid by culturing or a culture medium which is sterilized, a culture medium after completion of culturing or a culture medium which is sterilized, or cultured microbial cells collected from a culture medium mentioned above, or from dried microbial cells. When a liquid medium is used, the highly unsaturated fatty acids are recovered by, for example, the procedures explained below.

After completion of culturing, cultured microbial cells are obtained from the cultured medium by conventional solid-liquid separation procedures such as centrifugal separation and/or filtering. The microbial cells are preferably washed with water, crushed, and dried. Drying can be conducted by freeze drying, air drying, or the like procedure. The dried microbial cells are extracted with organic solvent preferably in a nitrogen stream. Examples of the organic solvent include ether, hexane, methanol, ethanol, chloroform, dichloromethane and petroleum ether. Moreover, excellent results can be obtained when the dried microbial cells are alternately extracted with methanol and petroleum ether, or when they are extracted with a chloroform-methanol-water single phase system. Extraction is conducted preferably with hexane.

A lipid containing the highly unsaturated fatty acids at high concentrations can be obtained by distilling the organic solvent off the extract under reduced pressure. Wet microbial cells can also be extracted in place of the procedures as mentioned above. When the wet microbial cells are used, a solvent such as methanol or ethanol which is miscible with water, or a solvent mixture of these solvents with water and/or other solvents which is miscible with water is used. The other procedures are the same as those mentioned above.

A lipid obtained by such procedures as mentioned above contains various highly unsaturated fatty acids as lipid compounds, for example, as constituent components of the fat. Although these compounds can be directly separated, it is preferred to separate these compounds as esters of a lower alcohol such as methyl dihomo-γ-linolenate, methyl arachidonate and methyl eicosapentaenoate. As a result of such esterification, the unsaturated fatty acids can be easily separated from other lipid components, and they can also be easily separated from other fatty acids formed during culturing such as palmitic acid and oleic acid (which are also esterified during esterification of the highly unsaturated fatty acids). For example, in order to obtain the highly unsaturated fatty methyl esters, the extracted lipid is preferably treated with an anhydrous methanol-hydrochloric acid (5-10%) mixture, a $BF_3$-methanol (10-50%) mixture, or the like, at room temperature for 1 to 24 hours.

In order to recover highly unsaturated fatty methyl esters from a reaction mixture, the reaction mixture is preferably extracted with an organic solvent such as hexane, ether or ethyl acetate. The extract is then dried over anhydrous sodium sulfate, etc., and the organic solvent is distilled off preferably under reduced pressure to give a mixture mainly containing fatty esters. The mixture of the fatty esters thus obtained contains fatty methyl esters such as methyl palmitate, methyl stearate, methyl oleate and methyl γ-linolenate in addition to the desired highly unsaturated fatty methyl esters.

In order to isolate the highly unsaturated fatty methyl esters from the mixture of these fatty methyl esters, namely, in order to isolate methyl dihomo-γ-linolenate, methyl arachidonate and methyl eicosapentaenoate which are desired compounds, column chromatography, low temperature crystallization, urea inclusion, liquid-liquid countercurrent chromatography, or the like procedure can be used singly or in combination.

In order to obtain a highly unsaturated fatty acid from each of the highly unsaturated fatty methyl esters thus isolated, the methyl ester is hydrolyzed with alkali, and then the resultant mixture is extracted with an organic solvent such as ether or ethyl acetate.

Furthermore, when the highly unsaturated fatty acids are not to be recovered via corresponding methyl esters, the above extracted lipid is subjected to alkaline fission (for example, with 5% sodium hydroxide at room temperature for 2 to 3 hours), and the fatty acids can be extracted from the fission solution and purified by a conventional procedure of extraction and purification of fatty acids.

The lipid obtained by culturing the microorganism of the present invention belonging to the genus *Mortierella* and having resistance to a carbon source of high concentration can be utilized for various types of products such as animal feeds or foods. When the lipid is used for the products, the lipid having been recovered from the cultured microbial cells or lipid obtained by purifying the former lipid can be used. The following materials can also be used: a culture medium in the course of producing the lipid by culturing the microbial cells, or a culture broth obtained by sterilizing the former culture solution; a culture broth after completion of the culturing, or a culture broth obtained by sterilizing the former culture broth; cultured microbial cells collected from any of the aforementioned cultured media, or dried products of the cultured microbial cells; or a residue which contains fat and oil and which is obtained after collecting the fat and oil from the aforementioned culture solutions or microbial cells.

The present invention relates to animal feed blended with microbial cells of the microorganism of the present invention. Examples of the animal feed of the present invention include pet food such as dog food and cat food, feed for poultry such as chickens, feed for farm animals such as pigs and cattle, and feed for pisciculture. Moreover, the microbial cells of the microorganism having produced and accumulated the lipid are preferred because the lipid is protected within the microbial cells so that it is difficult to oxidize and it is stabilized against heat sterilization. The residue obtained after recovering lipid from the cultured microbial cells is also preferred because it contains protein, ash, hydrocarbons, etc., in addition to the lipid of the present invention. In addition, the animal feed can also be prepared by processing a combination of the microbial cells of the microorganism in the present invention and other raw materials.

Furthermore, the microbial cells of the microorganism in the present invention and the lipid obtained therefrom can also be used as additives for animal feed.

Still furthermore, the microbial cells or cultured broth having produced and accumulating the lipid can also be used as feed for microorganism for feed. The microorganism for feed (zooplankton such as rotifer and brine shrimp) has heretofore been used for the production of feed (larva and juvenile) in aquaculturing fishes and shell fishes and crustacea. In order to aquaculture larva and juvenile, the microorganism must be aquacultured at first. When such a microorganism is to be aquacultured, the feed to be given to the microorganism for feed is determined by taking into consideration the nutritious requirement of the larva and juvenile which are to take the microorganism. Giving the cultured microbial cells or culture solution containing the lipid to the microorganism for food results in obtaining a microorganism for food containing arachidonic acid, dihomo-γ-linolenic acid and/or eicosapentaenoic acid and satisfying the nutrition requirement of larva and juvenile.

In addition, feed containing the microorganism for food can also be used for feed for fishes and shell fishes.

The lipid obtained in the present invention can be utilized for the production of poultry eggs enriched with arachidonic acid, dihomo-γ-linolenic acid and/or eicosapentaenoic acid as well as for the production of yolk oil enriched therewith. The poultry eggs enriched therewith are produced by feeding the poultry for collecting eggs, chickens in particular, with the animal feed as mentioned above. Moreover, the yolk oil enriched therewith is obtained by conventionally extracting fat and oil from the poultry eggs, the yolk in particular. Furthermore, the yolk oil can also be added to adjusted milk for infants, adjusted milk for immature infants, baby food and food for pregnant women and nursing mothers.

The lipid obtained in the present invention can also be utilized for such food containing lipid, preferably triglyceride oil as adjusted milk for infants, adjusted milk for immature infants, baby food, food for pregnant women and nursing mothers, food for aged people, nutrition-assisting food and healthy food. The food of the present invention is aimed at replenishing the nutrition with arachidonic acid, dihomo-γ-linolenic acid and/or eicosapentaenoic acid, and used for maintaining the health, etc. The form can be solid food, liquid food or a luxury.

Examples of food containing fat and oil include natural food containing fat and oil such as meat, fish and nuts, food prepared by adding fat and oil during cooking such as Chinese dishes, Chinese noodles and soup, food prepared by using fat and oil as a heating medium such as Japanese fries, fries, fried beancurd, frizzled rice, doughnuts and fried dough-cake, fat and oil food or processed food prepared by adding fat and oil during the preparation such as butter, margarine, mayonnaise, dressing, chocolate, instant Chinese noodles, caramels, biscuits, cookies, cake and ice cream, and food prepared by spraying or applying fat and oil during finish processing such as rice cake cubes and bean-jam buns. Application of the lipid is not limited to food containing fat and oil. Examples of the food include agricultural food such as bread, noodles, cooked rice and confectionery (candy, chewing gum, GUMI, tablet cake, Japanese confectionery) and bean curd and its processed products, fermented food such as sake, medical sake, sweet sake, vinegar, soy sauce and bean paste, food of live-stock products such as yogurt, ham, bacon and sausage, aquatic foods such as boiled fish-paste, fried fish balls and cake of pounded fish, and drinks such as fruit drinks, soft drinks, sports drinks, alcoholic beverages and tea.

When the lipid of the invention is used for food, a given amount of the lipid is blended with a food raw material, and the mixture can be processed by a conventional production method. Although the blending amount differs depending on the shape of the tablets and the form and properties of the food, a preferred amount of the lipid is generally from 0.001 to 50% by weight based on the entire amount of food. However, there is no specific limitation on the amount.

Functional food containing lipid can also be prepared from the lipid obtained in the present invention. An object of the functional food is to display the biological activity function that arachidonic acid, dihomo-γ-linolenic acid and/or eicosapentaenoic acid have, and the functional food is food for recovering and maintaining a healthy state from the state of hypergasia or for preventing the hypergasia.

The lipid of the invention can also take the form of powder, granules, tablets, capsules, troches, internal liquid, suspensions, emulsion, syrup, drinks, intestinal eutrophics, or the like. Moreover, the lipid can also be used in the form of natural liquid food, semi-digested nutritious food, component nutritious food, and the like, which are prepared by blending the fatty acids of the present invention with, for example, protein (although protein such as milk protein, soybean protein or egg albumin which has a good amino acid balance and is highly nutritious is most widely used as the protein source, a mixture of amino acids is also used in addition to decomposed products of the proteins mentioned above, oligopeptide of allbumen and hydrolyzed products of soybean), saccharides, fat, trace elements, vitamins, emulsifiers, perfume, and the like. The lipid can also be prepared in the form of the drinks and food as mentioned above.

Using the lipid, functional food and nutrition-assisting food can be produced as drinks and food having the form of powder, granules, tablets, capsules, troches, internal liquid, suspensions, emulsion, syrup, drinks, natural liquid food, semi-digested nutritious food, component nutritious food, intestinal eutrophics, and the like. Any of the nutritious components or functional components can also be blended in combination with the lipid. Moreover, during cooking food to be supplied to a hospital under the control of a nutritionist obeying the direction of a doctor, food prepared therein by adding the lipid obtained by the present invention can also be provided to the patients requiring the supply of arachidonic acid, dihomo-γ-linolenic acid and/or eicosapentaenoic acid.

EXAMPLES

Next, the present invention will be concretely explained by making reference to examples.

Example 1

Evaluation of Resistance to Carbon Source

The following media (pH 6.3) each in an amount of 10 ml were placed in 50-ml Erlenmeyer flasks, respectively: (1) a medium containing 1% glucose and 0.5% yeast extract; (2) a medium containing 2% glucose and 1% yeast extract; (3) a medium containing 3% glucose and 1.5% yeast extract; (4) a medium containing 4% glucose and 2% yeast extract; (5) a medium containing 5% glucose and 2.5% yeast extract; and (6) a medium containing 8% glucose and 1.6% yeast extract. Each of the media was sterilized at 120° C. for 20 minutes.

The genus $Mortierella$, strain SAM 2197 (FERM BP-6261) was inoculated into a Czapek agar medium (0.2% $NaNO_3$, 0.1% $K_2HPO_4$, 0.05% $MgSO_4·H_2O$, 0.05% KCl, 0.001% $FeSO_4·7H_2O$, 3% sucrose and 2% agar, pH 6.0) slanted to give a spore formation slant. Eight milliliters of sterilized water was placed therein, and the mixture was agitated, followed by inoculating 100 μl of the spore solution into each of the media.

The microorganism was cultured at 28° C. for 6 days using a reciprocal shaker (110 rpm). After culturing, the microbial cells were recovered by filtering, washed with water sufficiently, and dried at 105° C. for 2 hours. The weight of the dried microbial cells was determined, and the growth level (g/L) was calculated. To 20 mg of the dried microbial cells thus obtained were added 2 ml of methylene chloride and 2 ml of an anhydrous methanol-hydrochloric acid (10%) mixture. The resultant mixture was treated at 50° C. for 3 hours so that esterification with a methyl group was effected. Extraction was conducted twice by adding 4 ml of n-hexane and 1 ml of water. The extraction procedure was conducted twice in total. The solvent in the extract was distilled off by a centrifugal evaporator at 40° C. in 1 hour. The fatty methyl esters thus obtained were analyzed by gas liquid chromatography. Table 1 shows the results thus obtained.

TABLE 1

| Concentration of glucose (%) | 1 | 2 | 3 | 4 | 5 | 8 |
|---|---|---|---|---|---|---|
| Concentration of yeast extract (%) | 0.5 | 1 | 1.5 | 2 | 2.5 | 1.6 |
| Growth level (g/L) | 5.17 | 8.98 | 14.16 | 20.22 | 24.93 | 25.13 |
| Amount of total fatty acids produced (mg/g-dried microbial cells) | 55.1 | 119.8 | 70.4 | 125.7 | 135.5 | 179.3 |
| Content of arachidonic acid (%) | 25.9 | 35.1 | 30.2 | 47.8 | 53.8 | 43.3 |
| Amount of arachidonic acid produced (g/L) | 0.07 | 0.38 | 0.30 | 1.22 | 1.82 | 1.95 |

It can be seen that the growth level was improved as the initial glucose concentration was increased, and that the microorganism had resistance to the carbon source of high concentration. Moreover, it is confirmed that the productivity of arachidonic acid was improved when the initial glucose concentration was at least 4%.

Example 2

Evaluation of Amount of Arachidonic Acid Produced with Initial Glucose Concentration Increased The following media (pH 6.3) each in an amount of 5 liters were placed in 10-liter jar fermenters, respectively: (1) a medium containing 6% glucose, 2% yeast extract, 0.2% soybean oil and 0.01% Adekanol; (2) a medium containing 8% glucose, 2% yeast extract, 0.2% soybean oil and 0.01% Adekanol; and (3) a medium containing 11% glucose, 2% yeast extract, 0.2% soybean oil and 0.01% Adekanol. Each of the media was sterilized at 120° C. for 30 minutes. One hundred milliliters of a preculture solution of the genus $Mortierella$, strain SAM 2197 (FERM BP-6261) was inoculated into each of the media, and culturing with aeration and agitation was conducted for 8 days at 28° C. at an aeration rate of 1 vvm with stirring at 300 rpm.

To each of the media was added 2.0% of glucose on the second, the third and the fourth day of culturing. After completion of culturing, the following amounts, per liter of respective media, of dried microbial cells were obtained from the media (1), (2) and (3), respectively, by the same operation as in Example 1: (1) 42.3 g; (2) 60.5 g; and (3) 83.1 g. Dried microbial cells in an amount of 20 mg was subjected to hydrolysis, esterification with a methyl group and extraction in the same manner as in Example 1, and the fatty methyl esters thus obtained was analyzed by gas liquid chromatography. As a result, the following proportions (%) of arachidonic acid to the all fatty acids were obtained: (1) 40.7; (2) 39.4; and (3) 41.7. The following amounts of arachidonic acid produced (amounts of arachidonic acid per respective media) were obtained: (1) 7.1 g L; (2) 9.8 g/L; and (3) 14.3 g/L. The amount of arachidonic acid produced was improved as the initial glucose concentration was increased. When the initial glucose concentration was 11%, the amount of arachidonic acid produced was improved to 14.3 g/L.

Example 3

Control for Examples 4 and 5

One hundred milliliters of a medium (pH 6.0) containing 6% glucose and 2% yeast extract was placed in a 500-ml Erlenmeyer flask, and sterilized at 120° C. for 20 minutes. One hundred microliters the spore solution of the genus *Mortierella*, strain SAM 2197 (FERM BP-6261) used in Example 1 was inoculated into the medium, and shaking culture was conducted at 28° C. for 8 days using a reciprocal shaker (110 rpm). After culturing, the microbial cells were recovered by filtering, washed with water sufficiently, and freeze dried to give 3,120 mg of dried microbial cells. Fat and oil was extracted from the microbial cells by Bligh & Dyer's extraction using a chloroform-methanol-water single phase system solvent. The amount was 624 mg.

Methyl esterification of the fat and oil was carried out by treating it with a mixture of anhydrous methanol-hydrochloric acid (10%) at 50° C. for 3 hours, and the esterified products were extracted with ether. The fatty methyl esters thus obtained were analyzed by gas liquid chromatography, and the following composition was obtained: 13.3% methyl palmitate, 6.1% methyl stearate, 15.7% methyl oleate, 7.2% methyl linolate, 4.3% methyl γ-linolenate, 4.7% methyl dihomo-γ-linolenate, and 42.1% methyl arachidonate. Eicosapentaenoic acid was not detected. The following production amounts per medium were obtained from the above composition by conversion: 0.29 g/L of dihomo-γ-linolenic acid, and 2.63 g/L of arachidonic acid.

The mixture of the fatty methyl esters was further separated by column chromatography, and fractions of methyl γ-linolenate, methyl dihomo-γ-linolenate and methyl arachidonate were fractionated, respectively. The solvent was distilled off each of the fractions by a rotary evaporator to give the following purified products: 24.1 mg of methyl γ-linolenate, 26.4 mg of methyl dihomo-γ-linolenate and 236.4 mg of methyl arachidonate.

Example 4

Production of Dihomo-γ-Linolenic Acid by Addition of A5 Desaturase Inhibitor

Two milliliters of a medium (pH 6.0) containing 6% glucose, 2% yeast extract and 2% sesame oil was placed in a 10-ml Erlenmeyer flask, and sterilized at 120° C. for 20 minutes. Fifty microliters of the spore solution of the genus *Mortierella*, strain SAM 2197 (FERM BP-6261) used in Example 1 was inoculated, and shaking culture was conducted at 28° C. for 8 days using a reciprocal shaker (150 rpm). After completion of culturing, filtering, washing with water, drying, hydrolysis, esterification with a methyl group and extraction were conducted in the same manner as in Example 1. The fatty methyl esters thus obtained were analyzed by gas liquid chromatography. As a result, production of the following products per medium was recognized: 31.2 g/L dried microbial cells, 1.41 g/L dihomo-γ-linolenic acid, and 0.87 g/L arachidonic acid. It is evident from the results that a large amount of dihomo-γ-linolenic acid was produced while production of arachidonic acid was inhibited by adding to the medium sesame oil acting as a Δ5 desaturase inhibitor.

Example 5

Production of Eicosapentaenoic Acid by Low Temperature Culturing

Two milliliters of a medium (pH 6.0) containing 6% of glucose and 2% of yeast extract was placed in a 10-ml Erlenmeyer flask, and sterilized at 120° C. for 20 minutes. Fifty microliters of the spore solution of the genus *Mortierella*, strain SAM 2197 (FERM BP-6261) used in Example 1 was inoculated into the medium, and shaking culture was conducted at 28° C. for 2 days using a reciprocal shaker (150 rpm). The culturing temperature was lowered to 12° C., and the culturing was further continued for 6 days. After completion of culturing, filtering, washing with water, drying, hydrolysis, esterification with a methyl group and extraction were conducted in the same manner as in Example 1. The fatty methyl esters thus obtained were analyzed by gas liquid chromatography.

As a result, it is confirmed that the following substances could be produced by low temperature culturing: 11.7% of methyl palmitate, 5.8% of methyl stearate, 12.1% of methyl oleate, 6.4% of methyl linolate, 4.7% of methyl γ-linolenate, 4.9% of methyl dihomo-γ-linolenate, 38.1% of methyl arachidonate and 6.1% of methyl eicosapentaenoate. That is, it is confirmed that eicosapentaenoic acid could be produced by low temperature culturing.

Reference to the deposited microorganism under the provision of PCT Rule 13 bis and the international depository authority
International Depository Authority
   Name: National Institute of Bioscience and Human-Technology Agency of Industrial Science and Technology
   Address: 1-3, Higashi 1-chome, Tsukuba-City, Ibaragi Prefecture, Japan 305
Deposited Microorganism
   Name: *Mortierella* sp. SAM 2197
   Deposit No.: FERM BP-6261
   Deposit Date: Mar. 3, 1997
What is claimed is:
1. A process for producing arachidonic acid or a lipid containing arachidonic acid comprising the steps of:
   (1) culturing a microrganism belonging to the genus *Mortierella* and subgenus *Mortierella* that is strain SAM 2197 FERM BP-6261 , in a medium having a carbon source concentration of at least 4% by weight at the start of culturing and the addition of at least an additional 6% by weight of carbon source during the culturing, thereby forming arachidonic acid or a lipid containing arachidonic acid;

(2) collecting the cultured cells; and (3) extracting arachidonic acid or a lipid containing arachidonic acid from the collected cells;

wherein the microganism produces arachidonic acid of at least about 7 g/L culture medium when cultured in a medium containing at least about 4% carbon source at the start of culturing and the addition of at least an additional 6% by weight of carbon source during the culturing, and at least about 2% nitrogen source at the start of culturing for 5 to 10 days with agitation and aeration.

2. The process for producing arachidonic acid or lipid containing arachidonic acid according to claim 1, wherein the carbon source concentration at the start of culturing is at least 8% by weight.

* * * * *